(12) United States Patent
Kanda et al.

(10) Patent No.: US 10,365,206 B2
(45) Date of Patent: Jul. 30, 2019

(54) SURFACE CONDITION MONITORING APPARATUS

(71) Applicants: JAPAN AEROSPACE EXPLORATION AGENCY, Chofu-shi, Tokyo (JP); Sentencia Corporation, Musashino, Tokyo (JP)

(72) Inventors: Atsushi Kanda, Chofu (JP); Kazutaka Tateyama, Kitami (JP); Yasuhiro Harada, Kitami (JP); Hirokazu Ohmae, Musashino (JP); Toshiko Miyake, Musashino (JP)

(73) Assignees: JAPAN AEROSPACE EXPLORATION AGENCY, Tokyo (JP); SENTENCIA CORPORATION, Tokyo (JP)

(*) Notice: Subject to any disclaimer, the term of this patent is extended or adjusted under 35 U.S.C. 154(b) by 0 days.

(21) Appl. No.: 15/711,385

(22) Filed: Sep. 21, 2017

(65) Prior Publication Data

US 2019/0086323 A1 Mar. 21, 2019

(51) Int. Cl.
*G08G 1/09* (2006.01)
*G01N 21/17* (2006.01)
(Continued)

(52) U.S. Cl.
CPC .......... *G01N 21/17* (2013.01); *B60W 40/06* (2013.01); *G01B 11/0633* (2013.01);
(Continued)

(58) Field of Classification Search
None
See application file for complete search history.

(56) References Cited

U.S. PATENT DOCUMENTS

| 9,557,846 | B2* | 1/2017 | Baharav | ................ G06F 3/0421 |
| 2016/0018339 | A1* | 1/2016 | Perkins | ............. G01N 33/1833 |
| | | | | 73/61.48 |

(Continued)

FOREIGN PATENT DOCUMENTS

| JP | 9-113636 A | 5/1997 |
| JP | 10-267837 A | 10/1998 |

(Continued)

OTHER PUBLICATIONS

Office Action dated Oct. 2, 2018, issued in counterpart Japanese Application No. 2015-050304, with English translation. (5 pages).

*Primary Examiner* — Julie B Lieu
(74) *Attorney, Agent, or Firm* — Westerman, Hattori, Daniels & Adrian, LLP

(57) ABSTRACT

Provided is a surface condition monitoring apparatus including: a transparent member; a transmission unit including a transmitter that transmits electromagnetic waves from one side of the transparent member toward the other side; and a reception unit including a receiver that detects the electromagnetic waves that enter the one side of the transparent member from the other side, the transmission unit and the reception unit being arranged such that the receiver detects scattered waves of the electromagnetic waves transmitted from the transmitter, that enter the one side from the other side, the transmission unit being configured to be capable of transmitting a plurality of electromagnetic waves having different wavelengths, and the reception unit being configured to detect intensities of the scattered waves of the electromagnetic waves at different positions.

10 Claims, 3 Drawing Sheets

(51) Int. Cl.
 G01B 11/06 (2006.01)
 G01N 21/47 (2006.01)
 B60W 40/06 (2012.01)
 G01V 8/12 (2006.01)
 *G01N 21/55* (2014.01)

(52) U.S. Cl.
 CPC .............. G01N 21/47 (2013.01); G01V 8/12 (2013.01); *B60G 2401/17* (2013.01); *G01N 2021/558* (2013.01)

(56) References Cited

U.S. PATENT DOCUMENTS

2016/0298955 A1* 10/2016 Perkins ................. E21B 47/123
2017/0072834 A1* 3/2017 Schmitz-Hubsch ......................... B60Q 1/0023
2017/0293812 A1* 10/2017 Itoh ....................... G01N 21/21
2018/0005005 A1* 1/2018 He ....................... G06K 9/0002

FOREIGN PATENT DOCUMENTS

JP 2000-258554 A 9/2000
JP 2000-258557 A 9/2000

\* cited by examiner

SURFACE CONDITION MONITORING APPARATUS

BACKGROUND

The present invention relates to a surface condition monitoring apparatus including a transparent member, a transmission unit including a transmitter that transmits electromagnetic waves from one side of the transparent member toward the other side, and a reception unit including a receiver that detects the electromagnetic waves that enter the one side of the transparent member from the other side, and to a surface condition monitoring apparatus favorable for detecting a state and level of snow coverage and freeze at an upper portion of the transparent member.

It is important to monitor ice accretion/snow accretion states of road surfaces and runway surfaces (hereinafter, referred to as "road surfaces") in terms of safety management.

Therefore, a technology of measuring a depth of snow coverage on a road surface using a reflection of ultrasonic waves from outside is well known, and a technology of measuring a state of snow coverage and the like using external microwaves is well known.

However, in a case of setting a monitoring apparatus outside (above etc.), securing of a setting space, an influence of a natural environment (snow, rain, wind, etc.) on the monitoring apparatus, a breakage of the monitoring apparatus itself due to collisions of external foreign materials and the like become a problem.

Further, due to an influence on safeties of takeoff and landing of aircrafts regarding airport runways, there is a large restriction in setting the monitoring apparatus itself above the runway or a periphery thereof.

Furthermore, also in monitoring an ice accretion/snow accretion state of a plane surface of an aircraft, it is extremely difficult to set the monitoring apparatus outside the plane in terms of airworthiness of aircrafts.

In this regard, there is known a monitoring apparatus that has solved the problem of setting a monitoring apparatus outside by burying, inside a road surface or structure, a transmission apparatus for electromagnetic waves including light while enabling the electromagnetic waves including light to be transmitted toward the surface, and setting a reception apparatus for detecting scattered waves of electromagnetic waves near the transmission apparatus buried inside the road surface or structure (see, for example, Japanese Patent Application Laid-open No. Hei 9-113636 (hereinafter, referred to as Patent Literature 1), Japanese Patent Application Laid-open No. Hei 10-267837 (hereinafter, referred to as Patent Literature 2), and Japanese Patent Application Laid-open No. 2000-258554 (hereinafter, referred to as Patent Literature 3)).

SUMMARY

The monitoring apparatus disclosed in Patent Literature 1 or the like detects reflected light of light transmitted from a transmission unit (light emitter 4) by a reception unit (light receiver 5) and compares a light reception level with a predetermined threshold value to turn on/off operations of a snow melting apparatus.

While it becomes possible to detect to a certain extent whether the snow coverage needs to be melted using this principle, it has been impossible to monitor a specific state of a snow coverage regarding a depth and quality.

The monitoring apparatus disclosed in Patent Literature 2 or the like detects reflectance of a plurality of electromagnetic waves (infrared rays) having different wavelengths by a sensor, and measures a moisture content of snow from those values.

While it becomes possible to acquire a certain amount of information regarding a snow coverage quality using this principle, it has been impossible to monitor a snow depth, distinguishably detect ice, water, dirt, and the like in addition to snow, and monitor a specific state regarding a quality.

The monitoring apparatus disclosed in Patent Literature 3 or the like detects an amount of natural light from outside by one of two reception units (quantity-of-light sensor 1), detects a light amount including reflected light of light transmitted from a transmission unit (illuminant 11) by the other one of the reception units, and determines whether there is a snow coverage from those two pieces of information.

While it becomes possible to determine whether there is a snow coverage using this principle, it has been impossible to monitor a specific state of a snow coverage regarding a depth and quality.

In this regard, to solve the problems described above, the present invention aims at providing a surface condition monitoring apparatus that can be buried into a road surface or structure and is capable of judging a presence/absence of snow and the like (snow, ice, water, dirt, etc.) locally adhered onto a surface of the road surface or structure and also monitoring a specific state of a snow coverage regarding a depth and quality.

According to the present invention, there is provided a surface condition monitoring apparatus including: a transparent member; a transmission unit including a transmitter that transmits electromagnetic waves from one side of the transparent member toward the other side; and a reception unit including a receiver that detects the electromagnetic waves that enter the one side of the transparent member from the other side, the transmission unit and the reception unit being arranged such that the receiver detects scattered waves of the electromagnetic waves transmitted from the transmitter, that enter the one side from the other side, the transmission unit being configured to be capable of transmitting a plurality of electromagnetic waves having different wavelengths, and the reception unit being configured to detect intensities of the scattered waves of the electromagnetic waves at different positions.

It should be noted that the "electromagnetic waves" used in the specification include visible light and light having a shorter wavelength.

According to the surface condition monitoring apparatus according to claim 1, the transmission unit is configured to be capable of transmitting a plurality of electromagnetic waves having different wavelengths, and the reception unit is configured to detect intensities of scattered waves of the electromagnetic waves at different positions. Accordingly, by detecting a one-dimensional or two-dimensional intensity distribution, it becomes possible to judge a presence/absence of snow and the like (snow, ice, water, dirt, etc.) locally adhered onto a surface of a road surface or structure, accurately extract only information related to the snow coverage, highly accurately and separately obtain a depth and quality using scattered waves at each of the different wavelengths, and monitor a specific state of a snow coverage regarding a depth and quality.

Moreover, by integrating the transmission unit and the reception unit, it becomes possible to miniaturize the entire apparatus, raise a degree of freedom in selecting a setting location, and also bury the apparatus into a road surface or structure and the like at necessary positions.

Further, by the miniaturization, it becomes possible to realize highly-accurate monitoring at necessary positions by local measurements instead of a measurement of an average surface state.

Furthermore, by burying the apparatus into the road surface or structure, and the like at necessary positions, it becomes possible to eliminate an influence of an external natural environment on monitoring accuracy and prevent a breakage or the like due to collisions of external foreign materials and the like.

With the configuration according to claim 2, by the transmission unit including a plurality of transmitters, it becomes possible to more easily transmit electromagnetic waves having different wavelengths.

Further, by the reception unit including a plurality of receivers, it becomes possible to more easily detect a one-dimensional or two-dimensional intensity distribution.

With the configuration according to claim 3, by the plurality of receivers being arranged at different positions, it becomes possible to detect a one-dimensional or two-dimensional intensity distribution in a wider area.

With the configuration according to claim 4, by the transmission unit including a transmission adjustment mechanism capable of changing at least one of a position and a posture, it becomes possible to obtain measurement resolution of higher accuracy by optimally transmitting electromagnetic waves according to a setting environment or a state of snow coverage and the like, and monitor a specific state of a snow coverage regarding a depth and quality with higher accuracy.

Moreover, by the reception unit including a reception adjustment mechanism capable of changing at least one of a position and a posture, it becomes possible to obtain measurement resolution of higher accuracy by optimally detecting a one-dimensional or two-dimensional intensity distribution of electromagnetic waves according to a setting environment or a state of snow coverage and the like, and monitor a specific state of a snow coverage regarding a depth and quality with higher accuracy.

With the configuration according to claim 5, by the transmission unit including a transmitter that transmits electromagnetic waves having a directivity, it becomes possible to suppress an influence of the electromagnetic waves that directly reach a detection unit from the transmission unit and monitor a specific state of a snow coverage regarding a depth and quality with higher accuracy.

As the transmitter that transmits electromagnetic waves having a directivity, there are a transmitter that transmits laser light or the like that has a directivity in electromagnetic waves themselves or a transmitter equipped with a directional filter such as a deflection plate and a collimator lens.

DETAILED DESCRIPTION OF EMBODIMENTS

As long as a surface condition monitoring apparatus according to the present invention includes: a transparent member; a transmission unit including a transmitter that transmits electromagnetic waves from one side of the transparent member toward the other side; and a reception unit including a receiver that detects the electromagnetic waves that enter the one side of the transparent member from the other side, the transmission unit and the reception unit are arranged such that the receiver detects scattered waves of the electromagnetic waves transmitted from the transmitter, that enter the one side from the other side, the transmission unit is configured to be capable of transmitting a plurality of electromagnetic waves having different wavelengths, the reception unit is configured to detect intensities of the scattered waves of the electromagnetic waves at different positions, and the apparatus can be buried into a road surface or structure and is capable of judging a presence/absence of snow and the like (snow, ice, water, dirt, etc.) locally adhered onto a surface of the road surface or structure and also monitoring a specific state of a snow coverage regarding a depth and quality, a specific embodiment thereof is not limited.

Figure 1:
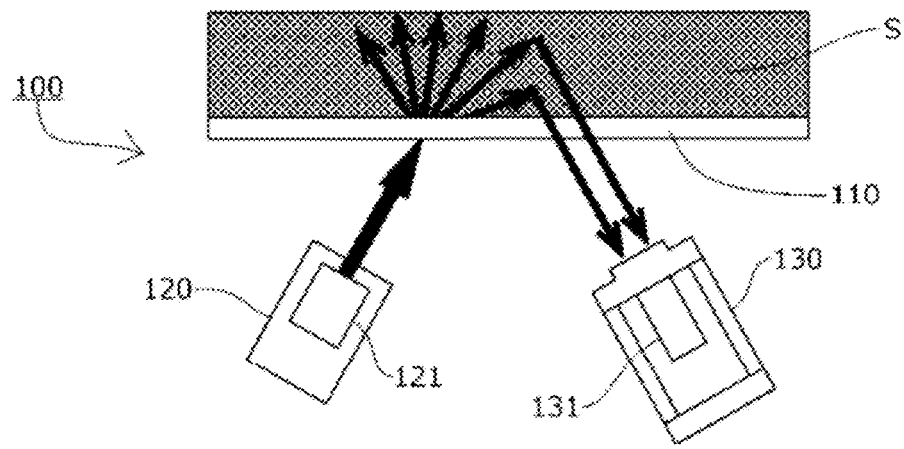
FIG. 1 is a schematic explanatory diagram of a snow ice monitoring apparatus according to the present invention.

As schematically shown in FIG. 1, a snow ice monitoring apparatus 100 according to a surface condition monitoring apparatus of the present invention includes a transparent member 110, a transmission unit 120 including a transmitter 121 that transmits electromagnetic waves from one side of the transparent member 110 toward the other side, and a reception unit 130 including a receiver 131 that detects the electromagnetic waves that enter the one side of the transparent member 110 from the other side. The transparent member 110 includes not only members that are transparent to visible light, that is, visually transparent, but also members that are electromagnetically transparent, that is, transmit electromagnetic waves while being visually opaque.

The transmitter 121 is, for example, a laser oscillator, and may be capable of transmitting laser light of a plurality of different wavelengths by itself, or a plurality of transmitters 121 may be attached to the transmission unit 120.

Moreover, it is also possible for at least one of a position and posture of the transmission unit 120 to be changed by a transmission adjustment mechanism, or at least one of a position and posture of the transmitter 121 to be changed by the transmission adjustment mechanism inside the transmission unit 120 while the transmission unit 120 is fixed.

The receiver 131 is, for example, a two-dimensional optical sensor such as a CCD, and may be capable of detecting a two-dimensional intensity distribution of scattered waves of the plurality of electromagnetic waves having different wavelengths by itself, or a plurality of receivers 131 may be attached to the reception unit 130 so that a one-dimensional or two-dimensional intensity distribution of scattered waves of the plurality of electromagnetic waves having different wavelengths is detected as a whole.

Moreover, it is also possible for at least one of a position and posture of the reception unit 130 to be changed by a reception adjustment mechanism, or at least one of a position and posture of the receiver 131 to be changed by the reception adjustment mechanism inside the reception unit 130 while the reception unit 130 is fixed.

In such a snow ice monitoring apparatus 100, a relationship between electromagnetic waves that enter from the transmitter 121 and electromagnetic waves detected by the receiver 131 with respect to a snow coverage S above the transparent member 110 differs depending on the wavelength.

Figure 2:
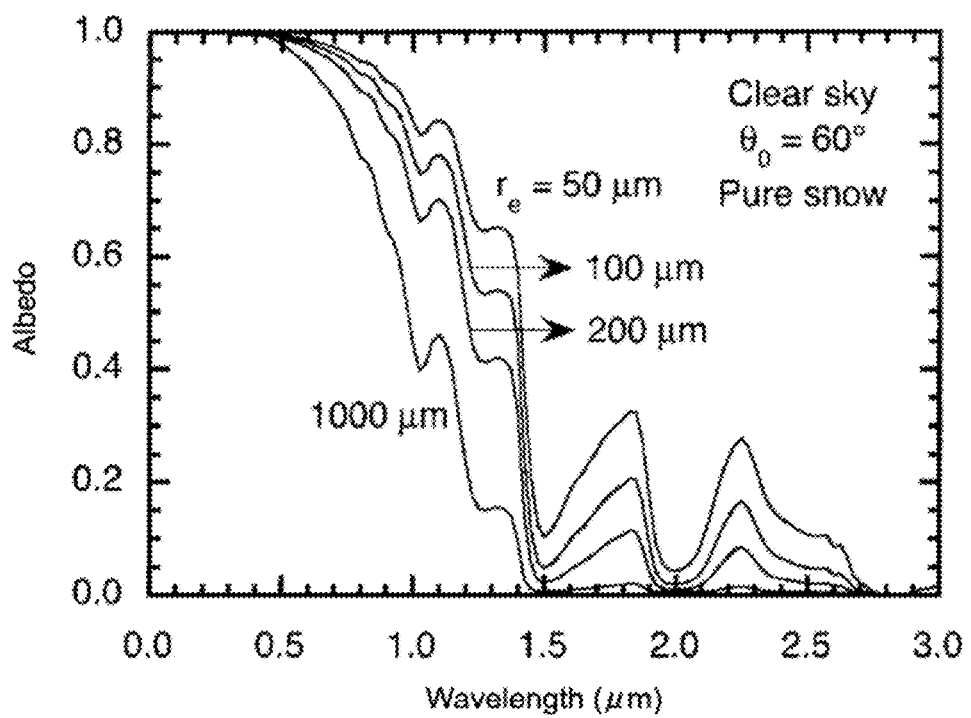
FIG. 2 is a graph of a snow coverage radiation transfer model.

As shown in FIG. 2, based on a snow coverage radiation transfer model, an albedo (ratio of reflected electromagnetic wave to incident electromagnetic wave) varies depending on the wavelength (re=50 μm in figure corresponds to fresh snow, and 100 μm corresponds to granular snow).

Accordingly, an amount of reflected/scattered electromagnetic waves largely differs with respect to a snow quality and wavelength, and a snow thickness and snow quality can be calculated from a reflection/scattering intensity relationship with respect to the wavelength of electromagnetic waves.

Then, by detecting a two-dimensional intensity distribution of scattered waves of the plurality of different electromagnetic waves by the receiver 131, a presence/absence of snow and the like (snow, ice, water, dirt, etc.) locally adhered above the transparent member 110 can be judged.

Further, an experiment of detecting differences in snow coverage amounts using scattered light intensities was carried out.

Figure 3:
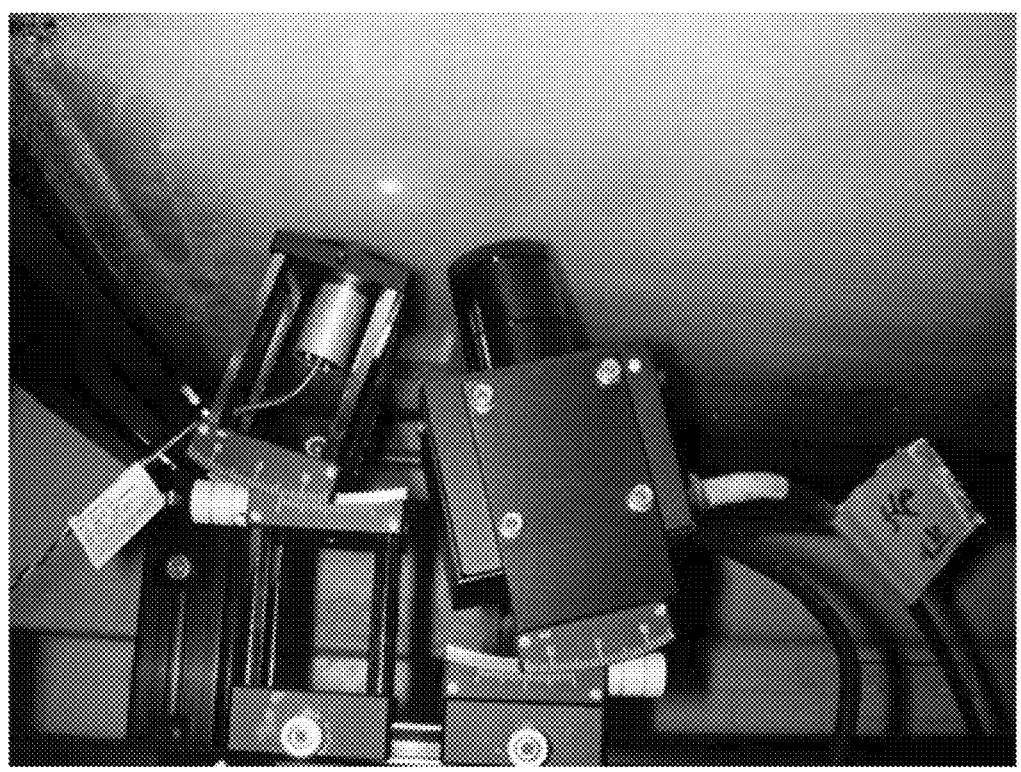
FIG. 3 is a reference photograph of an experimental example.

As shown in FIG. 3, in an experimental laboratory temperature-adjusted to −20°, a glass water tank was prepared as the transparent member 110, and the transmission unit and the reception unit were set below that.

The transmission unit and the reception unit were set on dedicated stages, and a mechanism capable of manually changing a distance between the units was provided.
two types of snow having different thicknesses (30 mm, 90 mm) were put in the water tank, laser was irradiated at an angle of 15° with respect to a vertical direction from the transmission unit below the water tank, and scattered light thereof was received by the reception unit at an angle of 15° with respect to the vertical direction, to thus measure an intensity.

Using this mechanism, a scattered light intensity distribution was also measured while varying the distance between the transmission unit and the reception unit from 0 mm to 60 mm.

Figure 4:
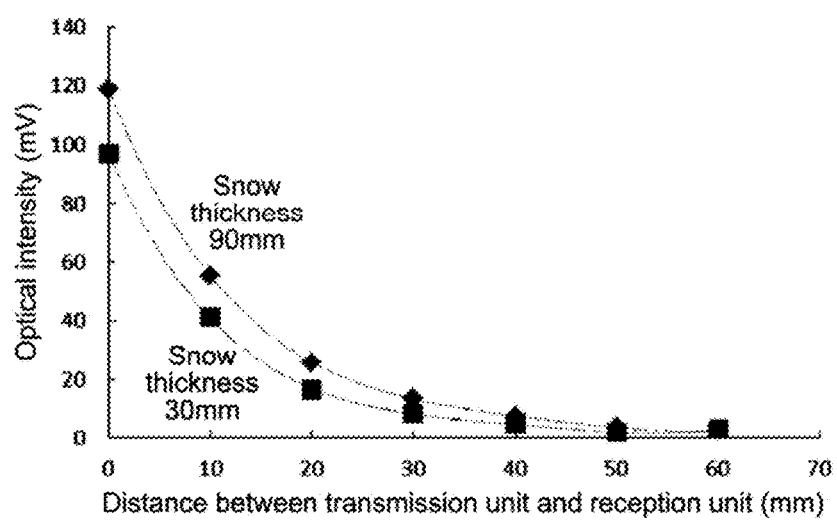
FIG. 4 is a graph of a measurement result of the experimental example.

The measurement result is as shown in FIG. 4, and thus it can be seen that the light intensity distribution differs depending on the snow thickness and a snow state can be detected by this apparatus.

As a result, according to the snow ice monitoring apparatus 100 of the present invention, it becomes possible to monitor a specific state of a snow coverage regarding a depth and quality.

Figure 5:
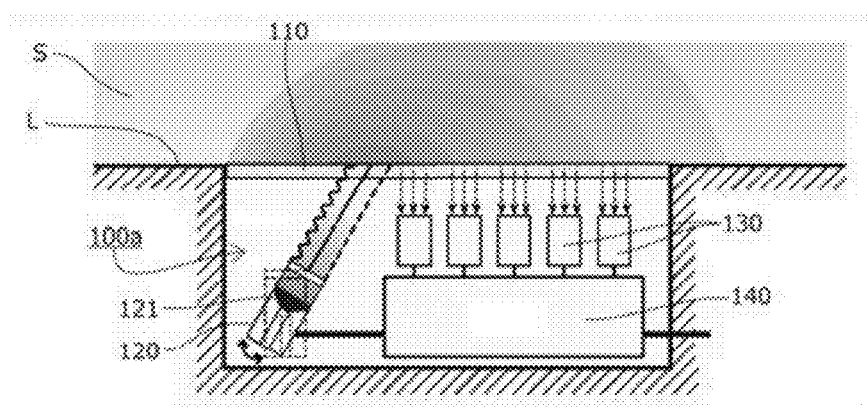
FIG. 5 is an explanatory diagram of a snow ice monitoring apparatus according to an embodiment of the present invention.

An example where the present invention is applied to a runway is shown in FIG. 5.

A snow ice monitoring apparatus 100a is set in an accommodation space provided in a runway L.

The transparent member 110 is set on the same plane as the runway L, the transmission unit 120 including the transmitter 121 is provided while being capable of changing a transmission angle with respect to the transparent member 110, and the reception units 130 each including the receiver 131 (not shown) are provided in 5 rows from the transmission unit 120 side while facing the transparent member 110.

A power supply/control unit 140 for the reception unit 130 and the transmission unit 120 is provided in the accommodation space and is configured to perform power supply from outside, posture control, detection signal outputs, and the like.

By providing one or a plurality of snow ice monitoring apparatuses 100a as described above at appropriate positions on the runway L, it becomes possible to monitor, without becoming an obstacle for aircrafts, a specific state of a snow coverage regarding a depth and quality of the entire runway while eliminating an influence of an external natural environment on monitoring accuracy and preventing a breakage or the like due to collisions of external foreign materials and the like.

The snow ice monitoring apparatus according to the present invention is not limited to the examples described above, and a setting location may also be other structures such as a road and a bridge or a mobile object such as an aircraft and a vehicle, and thus the present invention is applicable to various fields.

Furthermore, since a two-dimensional intensity distribution of scattered waves of a plurality of electromagnetic waves having different wavelengths is detected in the present invention, it is also possible to perform a detection, adherent pattern analysis, and the like of snow, ice, water, dirt, and the like in addition to a snow coverage, and the present invention is also applicable as a monitoring apparatus thereof.

The present invention may also take the following configurations.

The surface condition monitoring apparatus includes a control unit that calculates, based on a snow coverage radiation transfer model, a state of a snow coverage regarding a depth and quality on a front surface of the transparent member from signals corresponding to the intensities of the scattered waves detected by the receiver.

The surface condition monitoring apparatus includes a control unit that judges, based on a snow coverage radiation transfer model, whether a deposited material is locally adhered or adhered onto a front surface of the transparent member from signals corresponding to two-dimensional intensity distributions of the scattered waves detected by the receiver.

The surface condition monitoring apparatus includes the following transmitter and the receiver. The transmitter includes a laser transmitter that transmits laser light beams having difference wavelengths, and the receiver is a CCD (Charge-Coupled Device) sensor.

A surface condition monitoring apparatus includes a transparent member set to be on the same plane as an airport runway or taxiway; a transmission unit that is arranged in an accommodation space below the transparent member and transmits a plurality of electromagnetic waves having different wavelengths toward a ground surface side via the transparent member; and a reception unit that detects intensities of scattered waves derived from the electromagnetic waves that enter the accommodation space side from the ground surface side via the transparent member.

A surface condition monitoring system includes a plurality of surface condition monitoring apparatuses each including a transparent member set to be on the same plane as an airport runway or taxiway, a transmission unit that is arranged in an accommodation space below the transparent member and transmits a plurality of electromagnetic waves having different wavelengths toward a ground surface side via the transparent member, and a reception unit that detects intensities of scattered waves derived from the electromagnetic waves that enter the accommodation space side from the ground surface side via the transparent member. The plurality of surface condition monitoring apparatuses are each provided at different positions while being distributed within the airport runway or taxiway. The detected results of the plurality of surface condition monitoring apparatuses send one or more control units. The control unit calculates, based on a snow coverage radiation transfer model, a state of a snow coverage regarding a depth and quality on a front surface of the transparent member from signals respectively corresponding to the intensities of the scattered waves detected by the plurality of receivers. The control unit that judges, based on a snow coverage radiation transfer model, whether a deposited material is locally adhered onto a front surface of the transparent member from signals respectively corresponding to two-dimensional intensity distributions of the scattered waves detected by the plurality of receivers.

What is claimed is:

1. A surface condition monitoring apparatus, comprising:
    a transparent member;
    a transmission unit including a transmitter that transmits electromagnetic waves from one side of the transparent member toward the other side; and
    a reception unit including a receiver that detects the electromagnetic waves that enter the one side of the transparent member from the other side,
    the transmission unit and the reception unit being arranged such that the receiver detects scattered waves of the electromagnetic waves transmitted from the transmitter, that enter the one side from the other side,
    the transmission unit being configured to be capable of transmitting a plurality of electromagnetic waves having different wavelengths, and
    the reception unit being configured to detect one-dimensional, two dimensional, and a combination of one-dimensional and two-dimensional intensities of the scattered waves of the electromagnetic waves with different wavelengths,
    wherein the surface condition monitoring apparatus monitors the surface condition on the bases of a plurality of relationships between the transmitted electromagnetic waves and the detected one-dimensional, two dimensional, and a combination of one-dimensional and two-dimensional intensities.

2. The surface condition monitoring apparatus according to claim 1, wherein
    at least one of the transmission unit and the reception unit includes a plurality of transmitters or a plurality of receivers.

3. The surface condition monitoring apparatus according to claim 2, wherein
    the plurality of receivers are arranged at different positions.

4. The surface condition monitoring apparatus according to claim 1, wherein
    at least one of the transmission unit and the reception unit includes a transmission adjustment mechanism capable of changing at least one of a position and a posture or a reception adjustment mechanism capable of changing at least one of a position and a posture.

5. The surface condition monitoring apparatus according to claim 1, wherein
    the transmission unit includes a transmitter that transmits electromagnetic waves having a directivity.

6. The surface condition monitoring apparatus according to claim 1, further comprising
    a control unit that calculates, based on a snow coverage radiation transfer model, a state of a snow coverage regarding a depth and quality on a front surface of the transparent member from signals corresponding to the intensities of the scattered waves detected by the receiver.

7. The surface condition monitoring apparatus according to claim 1, further comprising
    a control unit that judges, based on a snow coverage radiation transfer model, whether a deposited material is locally adhered or adhered onto a front surface of the transparent member from signals corresponding to two-dimensional intensity distributions of the scattered waves detected by the receiver.

8. The surface condition monitoring apparatus according to claim 1, wherein
    the transmitter includes a laser transmitter that transmits laser light beams having difference wavelengths, and
    the receiver is a CCD (Charge-Coupled Device) sensor.

9. A surface condition monitoring apparatus, comprising:
    a transparent member set to be on the same plane as an airport runway or taxiway;
    a transmission unit that is arranged in an accommodation space below the transparent member and transmits a plurality of electromagnetic waves having different wavelengths toward a ground surface side via the transparent member; and
    a reception unit that detects one-dimensional, two dimensional, and a combination of one-dimensional and two-dimensional intensities of scattered waves derived from the electromagnetic waves that enter the accommodation space side from the ground surface side via the transparent member,
    wherein the surface condition monitoring apparatus monitors the surface condition on the bases of a plurality of relationships between the transmitted electromagnetic waves and the detected one-dimensional, two dimensional, and a combination of one-dimensional and two-dimensional intensities.

10. A surface condition monitoring system, comprising a plurality of surface condition monitoring apparatuses each including
    a transparent member set to be on the same plane as an airport runway or taxiway,
    a transmission unit that is arranged in an accommodation space below the transparent member and transmits a plurality of electromagnetic waves having different wavelengths toward a ground surface side via the transparent member, and
    a reception unit that detects one-dimensional, two dimensional, and a combination of one-dimensional and two-dimensional, intensities of scattered waves derived from the electromagnetic waves that enter the accommodation space side from the ground surface side via the transparent member,
    the plurality of surface condition monitoring apparatuses each being provided at different positions while being distributed within the airport runway or taxiway,
    wherein the surface condition monitoring apparatus monitors the surface condition on the bases of a plurality of relationships between the transmitted electromagnetic waves and the detected one-dimensional, two dimensional, and a combination of one-dimensional and two-dimensional, intensities.

* * * * *